(12) United States Patent
Greer et al.

(10) Patent No.: US 12,123,879 B2
(45) Date of Patent: Oct. 22, 2024

(54) HEAVY PEPTIDE APPROACH TO ACCURATELY MEASURE UNPROCESSED C-TERMINAL LYSINE

(71) Applicant: Regeneron Pharmaceuticals, Inc., Tarrytown, NY (US)

(72) Inventors: Tyler Greer, Elmsford, NY (US); Milos Cejkov, Ridgewood, NJ (US); Reid O'Brien Johnson, Hartsdale, NY (US); Xiaojing Zheng, Croton-on-the-Hudson, NY (US); Ning Li, New Canaan, CT (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 572 days.

(21) Appl. No.: 17/352,132

(22) Filed: Jun. 18, 2021

(65) Prior Publication Data

US 2021/0396764 A1 Dec. 23, 2021

Related U.S. Application Data

(60) Provisional application No. 63/041,015, filed on Jun. 18, 2020.

(51) Int. Cl.
*G01N 33/68* (2006.01)
*G01N 30/72* (2006.01)

(52) U.S. Cl.
CPC ..... *G01N 33/6848* (2013.01); *G01N 30/7233* (2013.01); *G01N 33/6854* (2013.01); *G01N 2440/00* (2013.01)

(58) Field of Classification Search
CPC . H01J 49/00; G01N 33/6848; G01N 33/6803; G01N 33/6851; G01N 33/6842; G01N 33/6854; G01N 30/7233; G01N 2440/00; G01N 2458/15
USPC ........................................ 250/281, 282, 288
See application file for complete search history.

(56) References Cited

U.S. PATENT DOCUMENTS

| | | | |
|---|---|---|---|
| 2013/0210051 A1* | 8/2013 | Louette | H01J 49/0009 435/23 |
| 2014/0364337 A1 | 12/2014 | Hermanson et al. | |
| 2020/0173960 A1* | 6/2020 | Iwamoto | G01N 33/6857 |
| 2020/0240998 A1* | 7/2020 | Yan | G01N 30/88 |

OTHER PUBLICATIONS

Gerber S A et al.: "Absolute quantification of proteins and phosphoproteins from cell lysates by tandem MS", Proceedings of the National Academy of Sciences, National Academy of Sciences, US, vol. 100, No. 12, Jun. 10, 2003 (Jun. 10, 2003), pp. 6940-6945.

(Continued)

*Primary Examiner* — Jason L McCormack
(74) *Attorney, Agent, or Firm* — Kramer Levin Naftalis & Frankel LLP (57) ABSTRACT

The present disclosure provides a method for accurately measuring post-translational modifications in proteins such as antibodies. In particular, the method pertains to the use of heavy isotopic standards to generate a calibration curve to allow for accurate quantitation of a modified peptide. The method may be used to accurately quantify C-terminal truncation in antibodies using mass spectrometry.

12 Claims, 5 Drawing Sheets

Specification includes a Sequence Listing.

(56) References Cited

OTHER PUBLICATIONS

Kirkpatrick D S et al.: "The absolute quantification strategy: a general procedure for the quantification of proteins and post-translational modifications", Methods, Academic Press, NL, vol. 35, No. 3, Mar. 1, 2005 (Mar. 1, 2005), pp. 265-273.

Greer Tyler et al.: "Integration of liquid chromatography mass spectrometry with a heavy peptide response curve accurately measures unprocessed C-terminal lysine during peptide mapping analysis of therapeutic antibodies in a single run", Journal of Pharmaceutical and Biomedical Analysis, vol. 197, Apr. 1, 2021 (Apr. 1, 2021), p. 113963.

Lawrence W. Dick et al.: "C-terminal lysine variants in fully human monoclonal antibodies: Investigation of test methods and possible causes", Biotechnology and Bioengineering, vol. 100, No. 6, Aug. 15, 2008 (2008-08-15), pp. 1132-1143.

International Search Report, International Application No. PCT/US2021/038136, Filing Date Jun. 18, 2021, Date of Mailing Oct. 15, 2021.

* cited by examiner

FIG. 2A  Δ4 Heavy SLSLSLGK Standard

FIG. 2B  Δ8 Heavy SLSLSLGK Standard

FIG. 2C  Δ12 Heavy SLSLSLGK Standard

FIG. 2D  Δ16 Heavy SLSLSLGK Standard

FIG. 2E  Δ4 Heavy SLSLSLG Standard.

HEAVY PEPTIDE APPROACH TO ACCURATELY MEASURE UNPROCESSED C-TERMINAL LYSINE

CROSS-REFERENCE TO RELATED APPLICATIONS

This application claims priority to and the benefit of U.S. Provisional Patent Application No. 63/041,015, filed Jun. 18, 2020 which is herein incorporated by reference.

SEQUENCE LISTING

The instant application contains a Sequence Listing which has been submitted electronically in ASCII format and is hereby incorporated by reference in its entirety. Said ASCII copy, created on Aug. 17, 2021, is named 070816-02601_SL.txt and is 1,177 bytes in size.

FIELD

This application relates to methods for identifying and quantifying a post-translational modification (PTM) in a protein of interest using heavy isotopic standards in liquid chromatography-mass spectrometry analysis.

BACKGROUND

Therapeutic monoclonal antibodies (mAbs) and bispecific antibodies (bsAbs) play a key role in treating many disorders. The advantages of this class of drugs, including high specificity and affinity to an expansive variety of molecular targets, warrant their continued development and have led to approvals for treatment of health conditions like asthma, rheumatoid arthritis, and elevated low density lipoprotein cholesterol, among many others. While the commercial and scientific success of therapeutic antibodies is unprecedented, their inherent benefits are tempered by their large size, complexity, and chemical heterogeneity, necessitating that a host of methods be used to evaluate their safety and efficacy.

A significant fraction of these methods is often devoted to evaluating post-translational modifications (PTMs), a product quality attribute and major source of mass and charge heterogeneity. The integration of highly sensitive mass spectrometer detectors with an ever-increasing number of liquid chromatography column chemistries and enzymatic treatment conditions has resulted in a mature suite of PTM characterization methods. A mass spectrometry (MS)-based peptide mapping assay allows for identification, localization, and quantification of all relevant PTMs with a detection limit of, for example, less than 0.1% under optimal conditions.

The advantages of PTM quantification by extracted ion chromatogram (XIC) are accompanied by some challenges that affect the method's accuracy and precision. Many of these issues are related to differences in the ionization of an unmodified peptide versus the modified form. For example, the C-terminal K truncation (des-K) value can be particularly impacted due to differences in ionization efficiencies and a reduction in the peptide's predominant charge state to 1+ compared to the unprocessed form (K, z=2+). The percent relative abundance of unprocessed C-terminal K is typically calculated in relation to the sum of K and des-K, but previous efforts have found that the percentage of K can be overestimated during peptide mapping quantification because, for example, the additional K on the C-terminus of the peptide sequence increases the ionization efficiency relative to the des-K peptide.

Some attempts to minimize this error include using only the most abundant charge state to calculate the XIC area under the curve (AUC) for each peptide, or using a correction factor determined by injecting equal molar amounts of each peptide onto the LC column and gauging the mass spectrometer response. However, while the first method may decrease the magnitude of the unprocessed C-terminal K value, it does so with no or little empirical knowledge of how much this value should be decreased by. The correction factor method assumes that the correction factor remains static across the possible concentration range of unprocessed C-terminal K, in the presence of potentially coeluting peptides, and among different mass spectrometers. Variation in these factors will lead to greater inaccuracies in the measurement processed versus unprocessed C-terminal K that may not be compensated for when using a static correction factor.

Thus, there exists a need for a method to accurately quantify the presence of a PTM in a protein of interest that corrects for differences in ionization efficiency of modified and unmodified peptides.

SUMMARY

The present invention provides methods for the accurate and precise characterization of PTMs in proteins, such as antibodies, using a heavy peptide approach. More specifically, the present disclosure provides methods for quantification of unprocessed C-terminal lysine (K) in antibodies. Methods of quantifying C-terminal K using a heavy peptide approach are provided.

In some exemplary embodiments, the method comprises (a) contacting a sample including said protein of interest to a digestive enzyme to obtain a peptide digest; (b) adding to said peptide digest a set of heavy peptide standards, wherein at least one heavy peptide standard includes said post-translational modification and at least one heavy peptide standard does not include said post-translational modification; (c) subjecting said peptide digest with said added heavy peptide standards to analysis using liquid chromatography-mass spectrometry to acquire a signal corresponding to each peptide of the peptide digest and heavy peptide standards; (d) generating a calibration curve using a relative signal of the at least one heavy peptide standard including said post-translational modification compared to the at least one heavy peptide standard not including said post-translational modification; (e) quantifying a post-translational modification of said protein of interest using the relative signal of at least one peptide from said protein of interest including said post-translational modification compared to at least one peptide from said protein of interest not including said post-translational modification; and (f) correcting the result of (e) using the calibration curve of (d) to further quantify said post-translational modification of said protein of interest.

In one aspect, the protein of interest is a therapeutic protein. In a specific aspect, said therapeutic protein is selected from a group consisting of an antibody, a soluble receptor, an antibody-drug conjugate, and an enzyme.

In one aspect, said protein of interest is a monoclonal antibody. In another aspect, said protein of interest is a bispecific antibody.

In one aspect, said post-translational modification is the presence of an unprocessed C-terminal lysine.

In one aspect, said heavy peptide standards are present at molar ratios between about 1:1 and about 1:1000 relative to at least one other heavy peptide standard. In another aspect, said heavy peptide standards comprise between about 1 and about 16 heavy isotopes. In a further aspect, said heavy peptide standards comprise $C^{13}$, $N^{15}$, or a combination thereof.

In one aspect, said digestive enzyme is trypsin.

In one aspect, said liquid chromatography method comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, said mass spectrometer is an electrospray ionization mass spectrometer, nano-electrospray ionization mass spectrometer, such as an Orbitrap mass spectrometer, a Q-TOF mass spectrometer or a triple quadruopole mass spectrometer, wherein said mass spectrometer is coupled to said liquid chromatography system, and wherein said mass spectrometer is capable of performing LC-MS, LC-MRM-MS, and/or LC-MS/MS analyses.

The present disclosure additionally provides kits for carrying out the method of the present invention. In some exemplary embodiments, the kit comprises a first composition including at least one heavy peptide standard including a post-translational modification; and a second composition including at least one heavy peptide standard not including said post-translational modification, wherein a relative signal of the at least one heavy peptide standard including said post-translational modification compared to the at least one heavy peptide standard not including said post-translational modification can be used to generate a calibration curve when analyzed by mass spectrometry, wherein said calibration curve can be used to quantify a post-translational modification of a protein of interest.

In one aspect, said post-translational modification is the presence of an unprocessed C-terminal lysine.

In one aspect, said heavy peptide standards are present at molar ratios between about 1:1 and about 1:1000 relative to at least one other heavy peptide standard. In another aspect, said heavy peptide standards comprise between about 1 and about 16 heavy isotopes. In a further aspect, said heavy peptide standards comprise $C^{13}$, $N^{15}$, or a combination thereof.

In one aspect, the kit further comprises at least one light peptide standard.

In one aspect, the compositions of the kit may be packaged either in aqueous media or in lyophilized form.

In one aspect, the compositions can be provided in a container. The container means of the kit will generally include at least one vial, test tube, flask, bottle, syringe or other container means, into which a component may be placed, and preferably, suitably aliquoted. In another aspect, the compositions of the kit may be provided as dried powder(s). When reagents and/or components are provided as a dry powder, the powder can be reconstituted by the addition of a suitable solvent. It is envisioned that the solvent may also be provided in another container means.

These, and other, aspects of the invention will be better appreciated and understood when considered in conjunction with the following description and accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 1A shows a schematic of the assay of the present invention according to an exemplary embodiment. A "clipped" peptide (corresponding to the C-terminus of a protein lacking a C-terminal lysine) is mixed with four "unclipped" peptides (corresponding to the C-terminus of a protein having a C-terminal lysine) to form a response curve (calibration curve) peptide mix. This response curve peptide mix is then mixed with a sample representing a potential antibody manufacturing sample (mAb Digest) to accurately quantitate the amount of C-terminal lysine present in the antibody sample. Figure discloses "SLSLSLG" as SEQ ID NO: 1 and "SLSLSLGK" as SEQ ID NO: 2.

FIGS. 2A-2E show the structures of four SLSLSLGK (SEQ ID NO:2) "unclipped" heavy peptides standards containing $^{13}C$ and $^{15}N$ isotopes (indicated by •), according to an exemplary embodiment. Isotopic heavy chain (HC) C-terminal peptide standards shown in FIGS. 2A-2D are Δ4, Δ8, Δ12, and Δ16 K peptides, respectively.

DETAILED DESCRIPTION

Therapeutic monoclonal antibodies (mAbs) and bispecific antibodies (bsAbs) play a key role in treating many disorders. The advantages of this class of drugs, including high specificity and affinity to an expansive variety of molecular targets, warrant their continued development and have led to approvals for treatment of health conditions like asthma, rheumatoid arthritis, and elevated low density lipoprotein cholesterol, among many others. While the commercial and scientific success of therapeutic antibodies is unprecedented, their inherent benefits are tempered by their large size, complexity, and chemical heterogeneity, necessitating that a host of methods be used to evaluate their safety and efficacy.

A significant fraction of these methods is devoted to evaluating PTMs, a product quality attribute and major source of mass and charge heterogeneity. The PTM complement of a single antibody is diverse, but common modifications are shared among almost all mAbs and bsAbs, such as C-terminal lysine truncation, glycosylation, N-terminal pyro-Glu formation, oxidation, amidation, deamidation, succinimide intermediate formation, glycation, isomerization, cysteinylation, and trisulfide bonding.

Careful monitoring of these PTM levels enables their control through predefined acceptance criteria and has become a common strategy for two distinct reasons. Firstly, numerous reports have shown that PTMs, especially when located in a complementarity determining region (CDR), can affect the stability and bioactivity of an antibody. Secondly, variability in PTM levels could indicate a lack of process control.

Post-translational modifications are assayed at the global level with chromatographic and electrophoretic techniques, including methods like size exclusion chromatography multi angle laser light scanning (SEC-MALLS), capillary electrophoresis sodium dodecyl sulfate (CE-SDS), imaged capillary isoelectric focusing (iCIEF), and cation exchange chromatography (CEX). Such methods have enjoyed wide acceptance, but typically identify only the most abundant modifications without determining their specific locations within the amino acid sequence.

For example, the acidic species in a CEX chromatogram will most likely contain PTMs like deamidation, glycation, and cysteinylation, and the basic species will be comprised of modifications like unprocessed C-terminal K, oxidation, and isomerization. However, as the amino acid locations of these PTMs are indeterminable in global analyses, it is challenging to determine if they are located in a CDR and at what abundance.

The integration of highly sensitive mass spectrometer detectors with an ever-increasing number of liquid chromatography column chemistries and enzymatic treatment conditions has resulted in a mature suite of PTM characterization methods. Intact mass analysis of an antibody via liquid chromatography mass spectrometry (LC-MS) does not yield site-specific PTM data, but it requires minimal sample preparation and can provide an analysis of larger PTMs with the additional benefit of mass identification.

Disulfide bond reduction and/or limited digestion with enzymes like IdeS, papain, GingisKHAN®, and FabALACTICA® marginally increase sample preparation time, but enable subunit level resolution of PTM localization that can be further increased by fragmenting each subunit using electron transfer dissociation (ETD) or another tandem mass spectrometry (MS/MS or $MS^2$) approach. However, site-specific localization and quantification of PTMs across a wide dynamic range are most commonly performed from the "bottom-up" using a technique called peptide mapping.

Peptide mapping methods require enzymatic digestion of the antibody, yielding a peptide mixture that is separated by liquid chromatography and detected by ultraviolet/visible (UV/Vis) absorbance before being ionized and infused into a mass spectrometer. Full MS spectra are acquired, and peptides are selected and fragmented to produce MS/MS spectra that are used to validate a peptide's identity or to localize a PTM on a peptide containing more than one potential modification site. While peptide mapping can potentially contribute preparation-related artifacts to the antibody sequence and significantly increases the time and complexity of an experiment, it is generally the most sensitive PTM characterization method as well as site specific.

Quantification of each modification can be performed using UV, or using extracted ion chromatograms (XICs) from mass spectrometry. UV quantification is obfuscated by coeluting peptides and is inherently less sensitive than modern mass spectrometers. Because of this, XIC-based quantification is routinely performed, and an MS-based peptide mapping assay allows for identification, localization, and quantification of all relevant PTMs with a detection limit of less than about 0.1% under optimal conditions.

The advantages of PTM quantification by XIC are accompanied by some unique challenges that affect the method's accuracy and precision. Many of these issues are related to differences in the ionization of an unmodified peptide versus the modified form for a number of potential reasons. There may be ion suppression of one or both peptide forms from coeluting peptide peaks. There may be a difference in solvent environment between the two peptide forms eluting at separate retention times. There may be a disparity in ionization efficiency between the modified peptide relative to the unmodified peptide. And, finally, there may be variability between mass spectrometers. Peptide mapping quantification of all PTMs is influenced by these factors, but C-terminal K truncation (des-K) quantification can be particularly impacted due to differences in ionization efficiencies and a reduction in the peptide's predominant charge state to 1+ compared to the unprocessed form (K), which has a predominant charge state of 2+.

C-terminal K truncation readily occurs because of carboxypeptidase activity during production from mammalian tissue culture cells. As a result, the predominant form in a recombinant mAb or bsAb is des-K. The percent relative abundance of unprocessed C-terminal K is typically calculated in relation to the sum of K and des-K. Unprocessed C-terminal K is not thought to be an efficacy or safety concern in antibodies since it is not in a CDR and has been shown to be rapidly lost upon injection with a half-life of roughly one hour. However, careful monitoring of this PTM demonstrates process control, and it has been reported that antibodies with more basic pI values may also have increased tissue uptake and blood clearance.

For these reasons, unprocessed C-terminal K measurement is still important, and previous efforts have found that the percentage of K may be overestimated during peptide mapping quantification because the additional K on the C-terminus of the peptide sequence increases the ionization efficiency relative to the des-K peptide.

Some attempts to minimize this error include using only the most abundant charge state to calculate the XIC area under the curve (AUC) for each peptide, or using a correction factor determined by injecting equal molar amounts of each peptide onto the LC column and gauging the mass spectrometer response. However, while the first method decreases the magnitude of the unprocessed C-terminal K value, it does so with no or little empirical knowledge of how much this value should be decreased by. The correction factor method assumes that the correction factor remains static across the possible concentration range of unprocessed C-terminal K, in the presence of potentially coeluting peptides, and among different mass spectrometers. Variation in these factors will lead to greater inaccuracies in the measurement processed versus unprocessed C-terminal K that may not be compensated for when using a static correction factor.

To address the challenges of accurately quantifying PTMs in recombinant proteins, for example unprocessed C-terminal lysine of a recombinant antibody, described herein are methods and kits for using heavy isotope peptide standards to generate a calibration curve to normalize detection differences between modified and unmodified peptides.

Figure 1A:
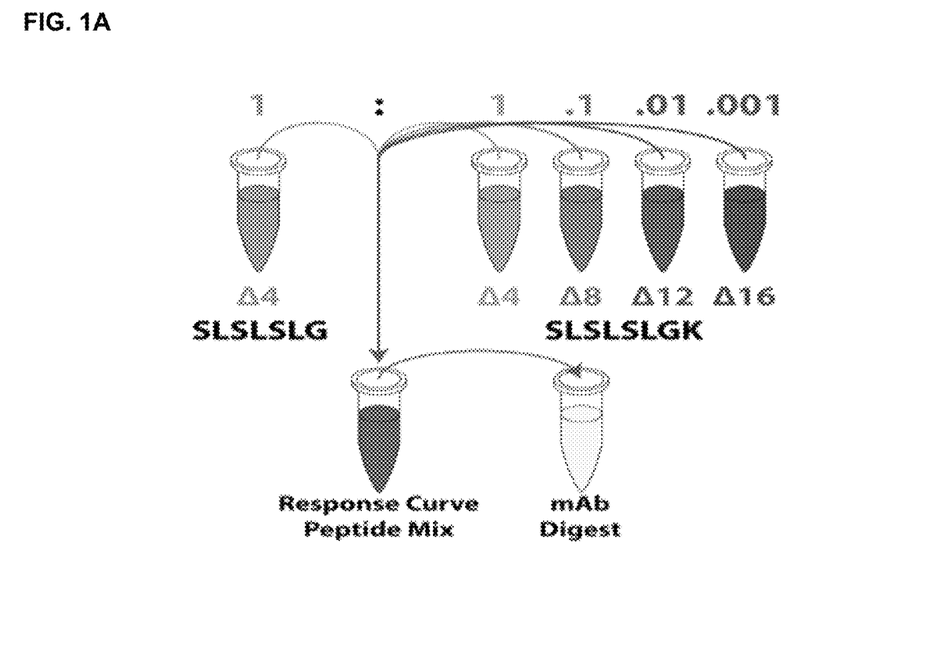
Figure 1B:
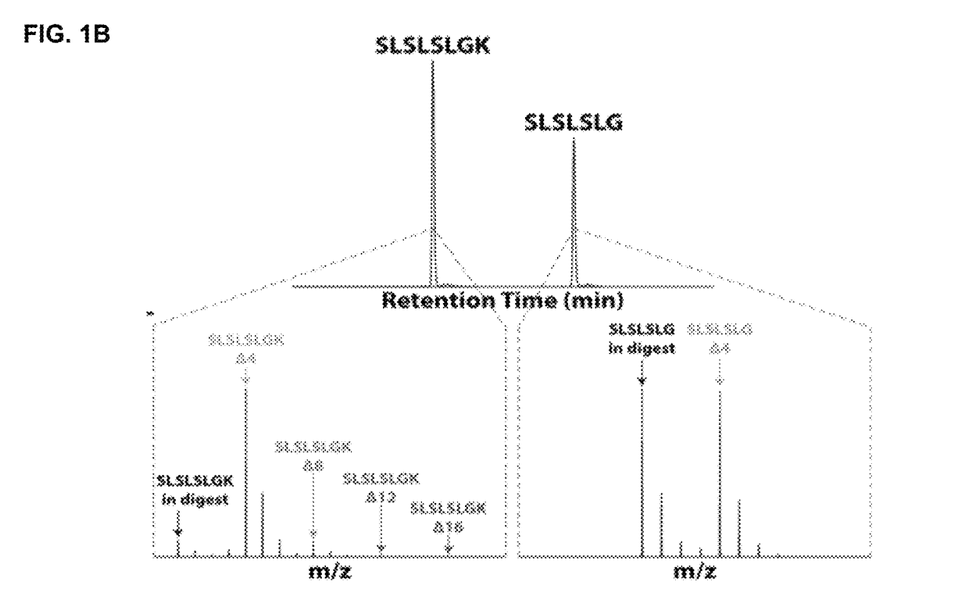
FIG. 1B shows the analytical peaks observed for each of the peptide species when subjected to liquid chromatography-mass spectrometry, according to an exemplary embodiment. Figure discloses "SLSLSLG" as SEQ ID NO: 1 and "SLSLSLGK" as SEQ ID NO: 2.
Figure 2A:
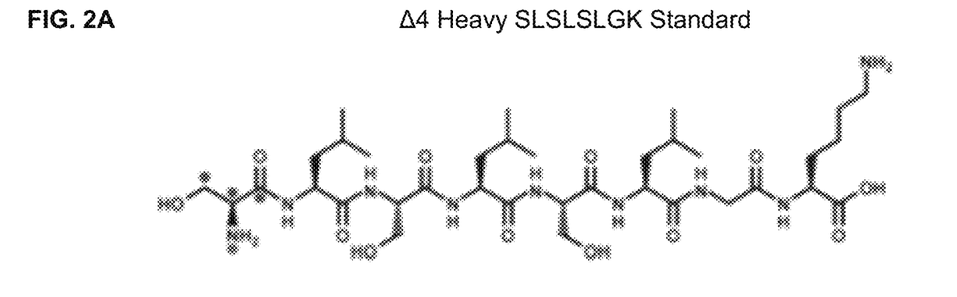
Figure 2B:
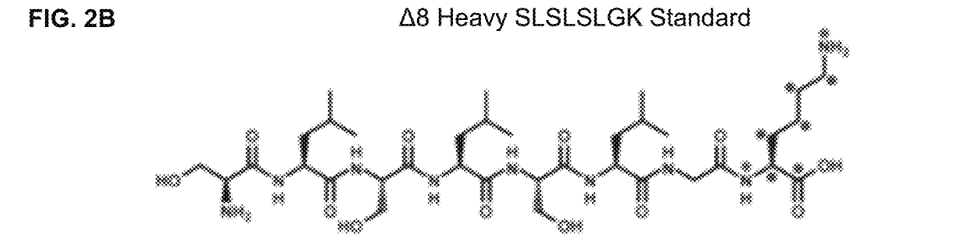
Figure 2C:
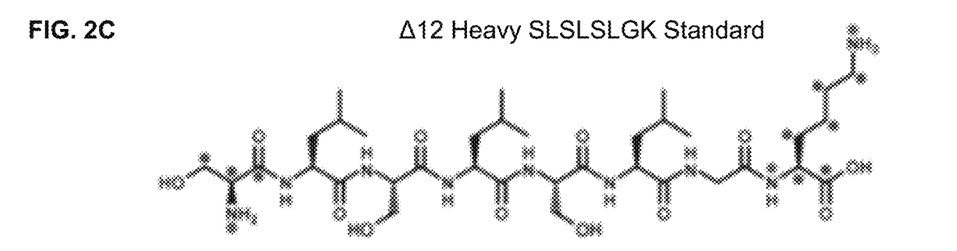
Figure 2D:
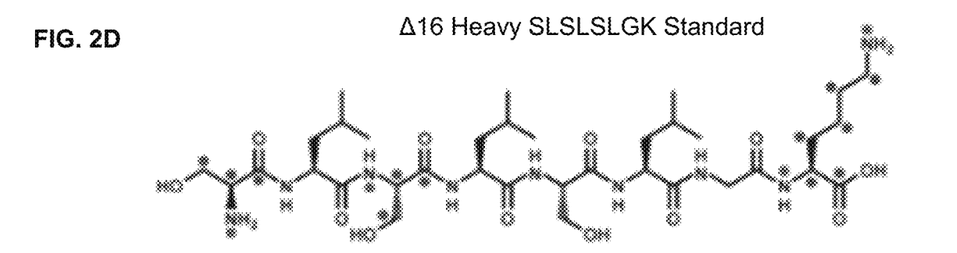
Figure 2E:
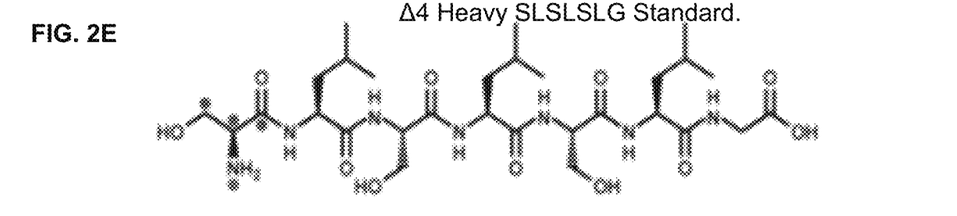
FIG. 2E illustrates the heavy SLSLSLG (SEQ ID NO:1) standard Δ4 des-K, containing $^{13}C$ and $^{15}N$ isotopes (indicated by •).

An exemplary embodiment of the invention is illustrated in FIG. 1A and FIG. 1B, where five heavy peptides are coincubated in the presence of an antibody digest to produce a detectable signal. The detectable signal can indicate an accurate measure of the "clipped" and "unclipped" C-terminal lysine (K).

The assay of the present invention, using a novel set of heavy peptides and analytical chemistries (for example, liquid chromatography and mass spectrometry) can be calibrated to provide highly accurate measurements. This assay fidelity is key for the manufacture of complex protein molecules, for example, therapeutic antibodies designed to be introduced into human patients.

The present invention also provides kits for carrying out the assay of the present invention. In an exemplary embodiment, a key step in the assay for determining accurate and true measures of the presence of a PTM, for example, C-terminal lysines (K), is the use of one or more heavy peptides of sufficient plurality such that, when admixed with appropriate standards and a sample, provide a readable signal. The signal is typically measured using analytical chemistries, for example, liquid chromatography-mass spectrometry (LC-MS).

Accordingly, exemplary components of a kit for carrying out the method of the present invention may include standard peptides without a PTM of interest, for example, "clipped" of a C-terminal lysine; standard peptides with a PTM of interest, for example, "unclipped"; standard heavy peptides ("clipped" and "unclipped") including, for example, one or more of the following exemplary peptides disclosed herein; and instructions for use, including, for example, instructions for calibration, data extraction, analysis, and interpretation.

Accordingly, the present invention provides for a convenient test kit and instructions for improving an important antibody manufacturing chemistry, manufacturing, and controls (CMC) endpoint.

It should be appreciated that the present invention provides for the accurate determination of the fine structure and exact amino acid sequence of a therapeutic protein, such as a therapeutic antibody. Accordingly, the present invention complements and improves the CMC (Chemistry, Manufacturing, and Controls) of any commercially produced therapeutic protein, such as a therapeutic antibody.

For example, the present invention allows for improving the manufacture and safeguarding of a number of antibody therapies. Such antibody therapies include: abciximab, adalimumab, adalimumab-atto, ado-trastuzumab emtansine, alemtuzumab, alirocumab, atezolizumab, avelumab, basiliximab, belimumab, bevacizumab, bezlotoxumab, blinatumomab, brentuximab vedotin, brodalumab, canakinumab, capromab pendetide, certolizumab pegol, cetuximab, daclizumab (Zenapax), daclizumab (Zinbryta), daratumumab, denosumab, dinutuximab, dupilumab, durvalumab, eculizumab, elotuzumab, evolocumab, golimumab, golimumab, ibritumomab tiuxetan, idarucizumab, infliximab, infliximab-abda, infliximab-dyyb, ipilimumab ixekizumab, mepolizumab, natalizumab, necitumumab, nivolumab, obiltoxaximab, obinutuzumab, ocrelizumab, ofatumumab, olaratumab, omalizumab, palivizumab, panitumumab, pembrolizumab, pertuzumab, ramucirumab, ranibizumab, raxibacumab, reslizumab, rituximab, secukinumab, siltuximab, tocilizumab, tocilizumab, trastuzumab, ustekinumab, vedolizumab, sarilumab, rituximab, hyaluronidaseguselkumab, inotuzumab ozogamicin, adalimumab-adbm, gemtuzumab ozogamicin, bevacizumab-awwb, benralizumab, emicizumab-kxwh, trastuzumab-dkst, infliximab-qbtx, ibalizumab-uiyk, tildrakizumab-asmn, burosumab-twza, and erenumab-aooe.

Other therapeutic antibodies of interest for various indications subject to the present invention include: aflibercept, for treating eye disorders; rilonacept, for treating blindness and metastatic colorectal cancer; alirocumab, for treating familial hypercholesterolemia or clinical atherosclerotic cardiovascular disease (ASCVD); dupilumab, for treating atopic dermatitis; sarilumab, for treating rheumatoid arthritis and COVID-19; cemiplimab, for treating PD-1 related disease; and antibodies for treating Ebola.

Unless described otherwise, all technical and scientific terms used herein have the same meaning as commonly understood by one of ordinary skill in the art to which this invention belongs. Methods and materials similar or equivalent to those described herein known to the skilled artisan can be used in the practice of particular embodiments described herein. All publications mentioned are hereby incorporated by reference in their entirety.

The term "a" should be understood to mean "at least one" and the terms "about" and "approximately" should be understood to permit standard variation as would be understood by those of ordinary skill in the art and where ranges are provided, endpoints are included. As used herein, the terms "include," "includes," and "including" are meant to be non-limiting and are understood to mean "comprise," "comprises," and "comprising" respectively.

As used herein, the term "protein" or "protein of interest" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may comprise one or multiple polypeptides to form a single functioning biomolecule. In another exemplary aspect, a protein can include antibody fragments, nanobodies, recombinant antibody chimeras, cytokines, chemokines, peptide hormones, and the like. A protein of interest can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. Proteins may be produced using recombinant cell-based production systems, such as the insect bacculovirus system, yeast systems (e.g., *Pichia* sp.), or mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Darius Ghaderi et al., Production platforms for biotherapeutic glycoproteins. Occurrence, impact, and challenges of non-human sialylation, 28 BIOTECHNOLOGY AND GENETIC ENGINEERING REVIEWS 147-176 (2012), the entire teachings of which are herein incorporated by reference). Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein of interest can be a recombinant protein, an antibody, a bispecific antibody, a multispecific antibody, antibody fragment, monoclonal antibody, fusion protein, scFv and combinations thereof.

As used herein, the term "recombinant protein" refers to a protein produced as the result of the transcription and translation of a gene carried on a recombinant expression vector that has been introduced into a suitable host cell. In certain exemplary embodiments, the recombinant protein can be an antibody, for example, a chimeric, humanized, or fully human antibody. In certain exemplary embodiments, the recombinant protein can be an antibody of an isotype selected from group consisting of: IgG, IgM, IgA1, IgA2, IgD, or IgE.

The term "antibody" as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains: CHL CH2 and CH3. Each light chain comprises a light chain variable region (abbreviated herein as LCVR or VL) and a light chain constant region. The light chain constant region comprises one domain: CL1. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-big-ET-1 antibody (or antigen-binding portion thereof) may be identical to the human germline sequences or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment comprises a sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively, or additionally, an antibody fragment may be wholly or partially synthetically produced. An antibody fragment may optionally comprise a single chain antibody fragment. Alternatively, or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The term "bispecific antibody" includes an antibody capable of selectively binding two or more epitopes. Bispecific antibodies generally comprise two different heavy chains with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions and such sequences can be expressed in a cell that expresses an immunoglobulin light chain.

A typical bispecific antibody has two heavy chains each having three heavy chain CDRs, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats such as, but not limited to, triomab, knobs into holes IgG (kih IgG), crossMab, orth-Fab IgG, Dual-variable domains Ig (DVD-Ig), two-in-one or dual action Fab (DAF), IgG-single-chain Fv (IgG-scFv), or κλ-bodies. The non-IgG-like different formats include tandem scFvs, diabody format, single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang & Mingju Hao, Bispecific antibodies and their applications, 8 JOURNAL OF HEMATOLOGY & ONCOLOGY 130; Dafne Müller & Roland E. Kontermann, Bispecific Antibodies, HANDBOOK OF THERAPEUTIC ANTIBODIES 265-310 (2014), the entire teachings of which are herein incorporated by reference). The methods of producing bsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated by reference: U.S. Ser. No. 12/823,838, filed Jun. 25, 2010; U.S. Ser. No. 13/488,628, filed Jun. 5, 2012; U.S. Ser. No. 14/031,075, filed Sep. 19, 2013; U.S. Ser. No. 14/808,171, filed Jul. 24, 2015; U.S. Ser. No. 15/713,574, filed Sep. 22, 2017; U.S. Ser. No. 15/713,569, field Sep. 22, 2017; U.S. Ser. No. 15/386,453, filed Dec. 21, 2016; U.S. Ser. No. 15/386,443, filed Dec. 21, 2016; U.S. Ser. No. 15/223,43 filed Jul. 29, 2016; and U.S. Ser. No. 15/814,095, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method.

As used herein, the term "multispecific antibody" refers to an antibody with binding specificities for at least two different antigens. While such molecules normally will only bind two antigens (i.e., bispecific antibodies, bsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The phrase "recombinant host cell" (or simply "host cell") includes a cell into which a recombinant expression vector coding for a protein of interest has been introduced. It should be understood that such a term is intended to refer not only to a particular subject cell but to a progeny of such a cell. Because certain modifications may occur in succeeding generations due to either mutation or environmental influences, such progeny may not, in fact, be identical to the parent cell, but are still be included within the scope of the term "host cell" as used herein. In an embodiment, host cells include prokaryotic and eukaryotic cells selected from any of the kingdoms of life. In one aspect, eukaryotic cells include protist, fungal, plant and animal cells. In a further aspect, host-cells include eukaryotic cells such as plant and/or animal cells. The cells can be mammalian cells, fish cells, insect cells, amphibian cells or avian cells. In a particular aspect, the host cell is a mammalian cell. A wide variety of mammalian cell lines suitable for growth in culture are available from the American Type Culture Collection (Manassas, Va.) and other depositories as well as commercial vendors. Cells that can be used in the processes of the invention include, but not limited to, MK2.7 cells, PER-C6 cells, Chinese hamster ovary cells (CHO), such as CHO-K1 (ATCC CCL-61), DG44 (Chasin et al., 1986, *Som. Cell Molec. Genet.*, 12:555-556; Kolkekar et al., 1997, *Biochemistry*, 36: 10901-10909; and WO 01/92337 A2), dihydrofolate reductase negative CHO cells (CHO/–DHFR, Urlaub and Chasin, 1980, *Proc. Natl. Acad. Sci. USA*, 77:4216), and dp12.CHO cells (U.S. Pat. No. 5,721,121); monkey kidney cells (CV1, ATCC CCL-70); monkey kidney CV1 cells transformed by SV40 (COS cells, COS-7, ATCC CRL-1651); HEK 293 cells, and Sp2/0 cells, 5L8 hybridoma cells, Daudi cells, EL4 cells, HeLa cells, HL-60 cells, K562 cells, Jurkat cells, THP-1 cells, Sp2/0 cells, primary epithelial cells (e.g., keratinocytes, cervical epithelial cells, bronchial epithelial cells, tracheal epithelial cells, kidney epithelial cells and retinal epithelial cells) and established cell lines and their strains (e.g., human embryonic kidney cells (e.g., 293 cells, or 293 cells subcloned for growth in suspension culture, Graham et al., 1977, 1 *Gen. Virol.*, 36:59); baby hamster kidney cells (BHK, ATCC CCL-10); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NY Acad. Sci.*, 383:44-68); MCR 5 cells; FS4 cells; PER-C6 retinal cells, MDBK (NBL-1) cells, 911 cells, CRFK cells, MDCK cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CV-1 cells, COS-1 cells, COS-3 cells, COS-7 cells, African green monkey kidney cells (VERO-76, ATCC CRL-1587; VERO, ATCC CCL-81); DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDM$_1$C$_3$ cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, Swiss/3T3 cells, Indian muntac cells, SIRC cells, Cu cells, and Jensen cells, or derivatives thereof) or any other cell type known to one skilled in the art.

As used herein, the term "therapeutic protein" refers to any protein that can be administered to a subject for the treatment of a disease or disorder. A therapeutic protein may be any protein with a pharmacological effect, for example, an antibody, a soluble receptor, an antibody-drug conjugate, or an enzyme.

As used herein, the term "liquid chromatography" refers to a process in which a biological/chemical mixture carried by a liquid can be separated into components as a result of differential distribution of the components as they flow through (or into) a stationary liquid or solid phase. Non-limiting examples of liquid chromatography include reverse phase liquid chromatography, ion-exchange chromatography, size exclusion chromatography, affinity chromatography, mixed-mode chromatography, hydrophobic chromatography or mixed-mode chromatography.

As used herein, the term "mass spectrometer" includes a device capable of identifying specific molecular species and measuring their accurate masses. The term is meant to include any molecular detector into which a polypeptide or peptide may be characterized. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends on the application.

In some exemplary embodiments, the mass spectrometer can be a tandem mass spectrometer. As used herein, the term "tandem mass spectrometry" includes a technique where structural information on sample molecules is obtained by using multiple stages of mass selection and mass separation. A prerequisite is that the sample molecules be transformed into a gas phase and ionized so that fragments are formed in a predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on, as long as one can obtain meaningful information, or the fragment ion signal is detectable. Tandem MS has been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device. The peptides identified by the mass spectrometer can be used as surrogate representatives of the intact protein and their post-translational modifications. They can be used for protein characterization by correlating experimental and theoretical MS/MS data, the latter generated from possible peptides in a protein sequence database. The characterization includes, but is not limited to, sequencing amino acids of the protein fragments, determining protein sequencing, determining protein de novo sequencing, locating post-translational modifications, or identifying post translational modifications, or comparability analysis, or combinations thereof.

As used herein, the term "database" refers to a compiled collection of protein sequences that may possibly exist in a sample, for example in the form of a file in a FASTA format. Relevant protein sequences may be derived from cDNA sequences of a species being studied. Public databases that may be used to search for relevant protein sequences included databases hosted by, for example, Uniprot or Swiss-prot. Databases may be searched using what are herein referred to as "bioinformatics tools". Bioinformatics tools provide the capacity to search uninterpreted MS/MS spectra against all possible sequences in the database(s), and provide interpreted (annotated) MS/MS spectra as an output. Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems.com//proteinpilot), Phenyx (www.phenyx-ms.com), Sorcerer (www.sagenresearch.com), OMS SA (www.pubchem.ncbi.nlm.nih.gov/omssa/), X!Tandem (www.thegpm.org/TANDEM/), Protein Prospector (prospector.ucsfedu/prospector/mshome.htm), Byonic (www.proteinmetrics.com/products/byonic) or Sequest (fields.scripps.edu/sequest).

In some exemplary embodiments, the mass spectrometer can be coupled to a liquid chromatography system. In some exemplary embodiments, the mass spectrometer can be coupled to a liquid chromatography-multiple reaction monitoring system. More generally, a mass spectrometer may be capable of analysis by selected reaction monitoring (SRM), including consecutive reaction monitoring (CRM) and parallel reaction monitoring (PRM).

As used herein, "multiple reaction monitoring" or "MRM" refers to a mass spectrometry-based technique that can precisely quantify small molecules, peptides, and proteins within complex matrices with high sensitivity, specificity and a wide dynamic range (Paola Picotti & Ruedi Aebersold, Selected reaction monitoring-based proteomics: workflows, potential, pitfalls and future directions, 9 NATURE METHODS 555-566 (2012)). MRM can be typically performed with triple quadrupole mass spectrometers wherein a precursor ion corresponding to the selected small molecules/peptides is selected in the first quadrupole and a fragment ion of the precursor ion was selected for monitoring in the third quadrupole (Yong Seok Choi et al., Targeted human cerebrospinal fluid proteomics for the validation of multiple Alzheimers disease biomarker candidates, 930 JOURNAL OF CHROMATOGRAPHY B 129-135 (2013)).

In some aspects, the mass spectrometer in the method or system of the present application can be an electrospray ionization mass spectrometer, nano-electrospray ionization mass spectrometer, or a triple quadrupole mass spectrometer, wherein the mass spectrometer can be coupled to a liquid chromatography system, wherein the mass spectrometer is capable of performing LC-MS (liquid chromatography-mass spectrometry) or LC-MRM-MS (liquid chromatography-multiple reaction monitoring-mass spectrometry) analyses.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion.

As used herein, the term "digestive enzyme" refers to any of a large number of different agents that can perform digestion of a protein. Non-limiting examples of hydrolyzing agents that can carry out enzymatic digestion include protease from *Aspergillus* Saitoi, elastase, subtilisin, protease XIII, pepsin, trypsin, Tryp-N, chymotrypsin, aspergillopepsin I, LysN protease (Lys-N), LysC endoproteinase (Lys-C), endoproteinase Asp-N(Asp-N), endoproteinase Arg-C(Arg-C), endoproteinase Glu-C(Glu-C) or outer membrane protein T (OmpT), immunoglobulin-degrading enzyme of *Streptococcus pyogenes* (IdeS), thermolysin, papain, pronase, V8 protease or biologically active fragments or homologs thereof or combinations thereof. For a recent review discussing the available techniques for protein digestion see Switazar et al., "Protein Digestion: An Overview of the Available Techniques and Recent Developments" (Linda Switzar, Martin Giera & Wilfried M. A. Niessen, Protein Digestion: An Overview of the Available Techniques and Recent Developments, 12 JOURNAL OF PROTEOME RESEARCH 1067-1077 (2013)).

The amount of digestive enzyme and the time required for digestion can be appropriately selected. When the enzyme to substrate ratio is unsuitably high, the correspondingly high digestion rate will not allow sufficient time for the peptides to be analyzed by mass spectrometer, and sequence coverage will be compromised. On the other hand, a low enzyme to substrate ratio would need a long digestion time and thus a long data acquisition time. The enzyme to substrate ratio can range from about 1:0.5 to about 1:200.

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage of glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). In an exemplary embodiment, a post-translational modification is cleavage of a lysine at a protein C-terminus. Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See European Bioinformatics InstituteProtein Information ResourceSIB Swiss Institute of Bioinformatics, EUROPEAN BIOINFORMATICS INSTITUTE DRS—DROSOMYCIN PRECURSOR—DROSOPHILA MELANOGASTER (FRUIT FLY)—DRS GENE & PROTEIN, http://www.uniprot.org/docs/ptmlist for a more detailed controlled vocabulary of PTMs curated by UniProt.

As used herein, the term "C terminal lysine (K)" or "K peptide" refers to an amino acid lysine residue or "K" residue that can be present or absent on the end of an amino acid sequence. In an exemplary embodiment, a C terminal lysine is on the heavy chain of an antibody. The term "truncated peptide" or "(des-K)" refers to a representative portion of a protein having the C-terminal amino acid sequence missing a C-terminal lysine (K).

As used herein, the term "unclipped" refers to a protein C-terminal sequence wherein the C-terminal sequence has a terminal lysine (K) amino acid residue. As used herein, the term "clipped" refers to a protein C-terminal sequence wherein the C-terminal sequence is missing a terminal lysine (K) amino acid residue.

As used herein, the term "analyzing and quantifying the percentage of K peptide" refers to comparing the difference between a first and second assay signal sufficient to ascertain the relative presence or absence of a C-terminal lysine of a protein sequence. In an exemplary embodiment, the protein sequence is an antibody heavy chain.

As used herein, the term "heavy peptides" refers to any peptide of the invention, or equivalents thereof, wherein at least one or more carbon or nitrogen atoms of the peptide is a heavy isotope thereof, for example, $^{13}$C and $^{15}$N isotopes.

As used herein, the term "peptide digest" refers to a mix of peptides resulting from contacting a protein with one or more enzymes capable of digesting a protein sequence. In an exemplary embodiment, a peptide digest includes a polypeptide sequence representative of the C-terminus of the digested protein.

It is understood that the present invention is not limited to any of the aforesaid protein(s) of interest, therapeutic protein(s), recombinant protein(s), recombinant host cell(s), antibody(s), liquid chromatography system(s), mass spectrometer(s), database(s), bioinformatics tool(s), digestive enzyme(s), post-translational modification(s), or heavy peptide(s), and any protein(s) of interest, therapeutic protein(s), recombinant protein(s), recombinant host cell(s), antibody(s), liquid chromatography system(s), mass spectrometer(s), database(s), bioinformatics tool(s), digestive enzyme(s), post-translational modification(s), or heavy peptide(s) can be selected by any suitable means.

The present invention will be more fully understood by reference to the following Examples. They should not, however, be construed as limiting the scope of the invention.

EXAMPLES

Materials and Methods.

The present invention, when practiced by the person skilled in the art, may make use of conventional techniques in the field of pharmaceutical chemistry, immunology, molecular biology, cell biology, recombinant DNA technology, and assay techniques, as described in, for example, Sambrook et al. "Molecular Cloning: A Laboratory Manual", 3$^{rd}$ ed. 2001; Ausubel et al. "Short Protocols in Molecular Biology", 5$^{th}$ ed. 1995; "Methods in Enzymology", Academic Press, Inc.; MacPherson, Hames and Taylor (eds.). "PCR 2: A practical approach", 1995; "Harlow and Lane (eds.) "Antibodies, a Laboratory Manual" 1988; Freshney (ed.) "Culture of Animal Cells", 4$^{th}$ ed. 2000; "Methods in Molecular Biology" vol. 149 ("The ELISA Guidebook" by John Crowther) Humana Press 2001, and later editions of these treatises (e.g., "Molecular Cloning" by Michael Green (4$^{th}$ Ed. 2012) and "Culture of Animal Cells" by Freshney (7$^{th}$ Ed., 2015), as well as current electronic versions.

Methods useful for quantifying and analyzing PTMs in proteins are provided within the disclosure. More specifically, the present disclosure provides methods for quantifying and analyzing C-terminal lysine (K) in proteins, for example, antibodies. The methods include applying a set of heavy C-terminal peptide standards to a digested protein. The protein may be digested by proteases such as trypsin and other suitable enzymes.

The method of the present invention may involve spiking calibration curves into antibody digests and injecting approximately equimolar amounts of heavy des-K peptide to digested des-K peptide onto a column in each LC-MS/MS run. Unprocessed C-terminal K may be quantified in a single LC-MS/MS peptide mapping experiment.

The method of the present invention may involve generating a calibration curve spanning a ratio range of about 1:1000-1:1 K to des-K peptide. The calibration curve may have an error of less than about 10%, less than about 9%, or less than about 8%.

Mass spectra may be quantified using various spectrometers, such as, for example, Thermo Q-Exactive Plus 3, Q-Exactive Plus 4 or Orbitrap Fusion Lumos mass spectrometers.

The following working examples demonstrate exemplary methods for identifying and quantifying PTMs in recombinant proteins.

Example 1. Assay Design and Methods for Calibration

This example shows the experimental design of the assay of the invention for generating a calibration curve to accurately assess the ratio of a peptide modified with a PTM and the same peptide without said PTM.

All light and heavy isotopic peptide standards were purchased from New England Peptide (Gardner, MA). Trifluoroacetic acid (TFA), formic acid (FA), tris [2-carboxylethyl] phosphine hydrochloride (TCEP-HCl), and Optima LC/MS grade acetonitrile (ACN) were obtained from Thermo Fisher Scientific (Rockford, IL) while glacial acetic acid and iodoacetamide (IAM) were procured from Sigma-Aldrich (St. Louis, MO). Sequencing grade modified trypsin, ultrapure urea, and ultrapure 1 M Tris(hydroxymethyl)aminomethane hydrochloride (Tris-HCl) were purchased from Promega (Madison, WI), Alfa Aesar (Haverhill, MA), and Invitrogen (Carlsbad, CA), respectively. Milli-Q water was purified by a Millipore Milli-Q Advantage A10 Water Purification System.

Isotopic HC C-terminal peptide standards were used to normalize the mass spectrometer response between corresponding light unprocessed and processed peptides. Peptide standards included SLSLSLG (SEQ ID NO:1), SLSLSLGK (SEQ ID NO:2), SLSLSPG (SEQ ID NO:3) and SLSLSPGK (SEQ ID NO:4).

Heavy isotopic SLSLSLGK (SEQ ID NO:2) standards are shown in FIG. 1. $^{13}$C and $^{15}$N are indicated by •. Δ4 (e.g., comprising 4 heavy isotopes of carbon or nitrogen), Δ8, Δ12, and Δ16 K peptides are shown in FIGS. 1A, 1B, 1C and 1D, respectively. The heavy isotopic SLSLSLG (SEQ ID NO:1) standard, Δ4 des-K, is shown in FIG. 2. $^{13}$C and $^{15}$N are indicated by •.

Figure 3:
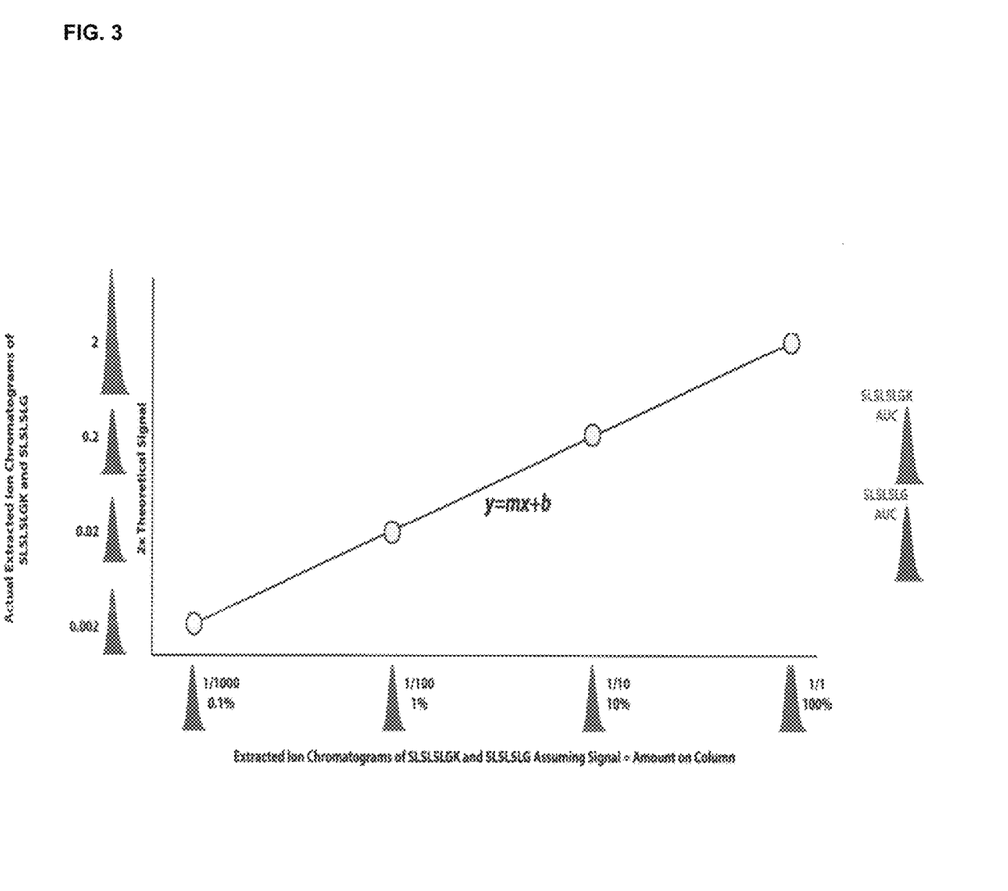
FIG. 3 shows a calibration curve (CC) exhibiting a proportional relationship between "clipped" and "unclipped" peptides according to an exemplary embodiment. Figure discloses "SLSLSLG" as SEQ ID NO: 1 and "SLSLSLGK" as SEQ ID NO: 2.

The peptide standards were dissolved in 10% ACN, 0.1% TFA and combined into two calibration curve sets according to the C-terminal sequence (LGK or PGK). Each set contained equimolar concentrations of Δ4 des-K and K peptide as well as Δ8, Δ12, and Δ16 K peptides at molar ratios of 1:10, 1:100, and 1:1000 K to des-K, respectively. The mixture was analyzed by XIC as shown in FIG. 3.

Figure 4:
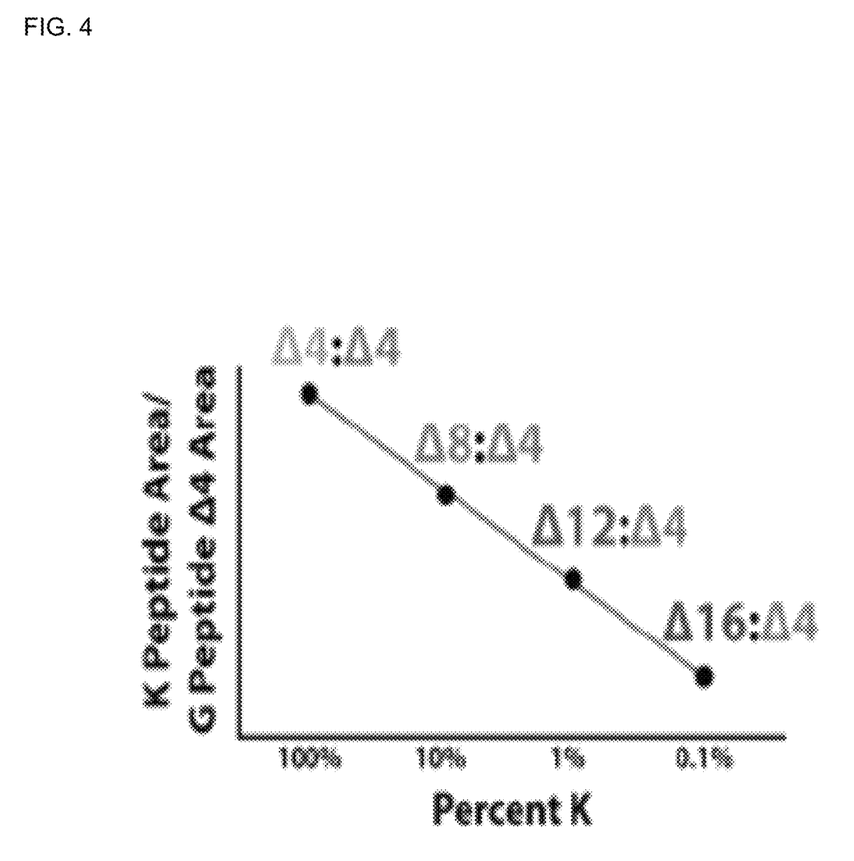
FIG. 4 shows an exemplary response curve using heavy chain (HC) C-terminal peptides according to an exemplary embodiment.
Figure 5A:
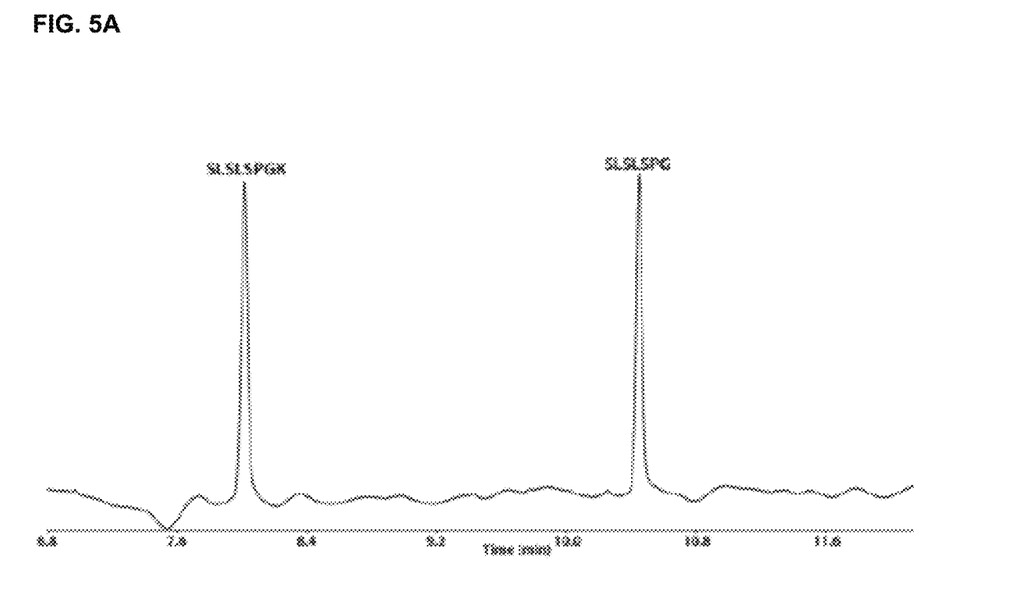
FIG. 5A shows a UV chromatogram of an equimolar mixture of "unclipped" SLSLSPGK (SEQ ID NO:4) and "clipped" SLSLSPG (SEQ ID NO:3) according to an exemplary embodiment.
Figure 5B:
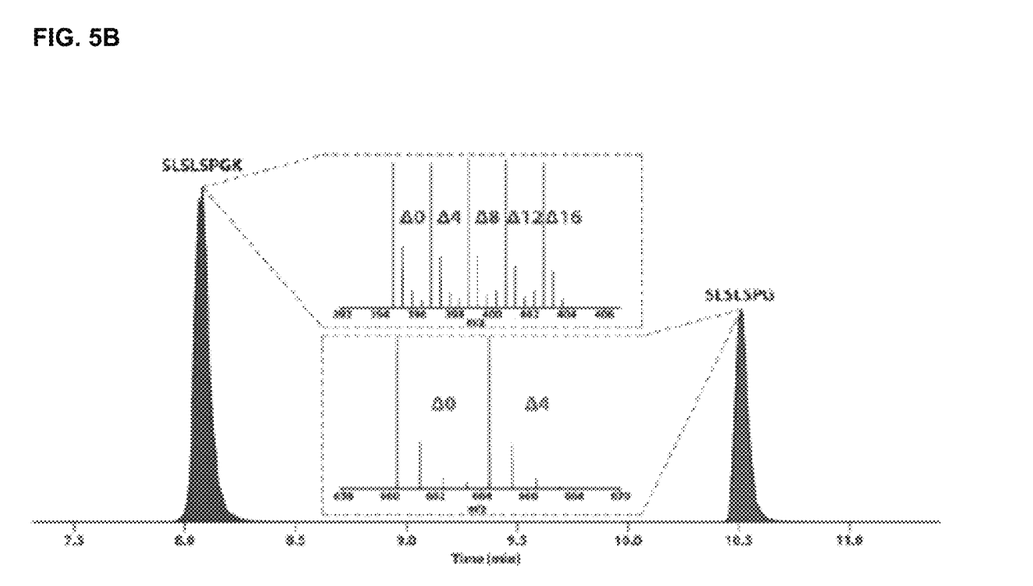
FIG. 5B shows an extracted ion chromatogram (XIC) of equimolar amounts of the SLSLSPGK (SEQ ID NO:4) and SLSLSPG (SEQ ID NO:3) reagent set according to an exemplary embodiment.

An equimolar mixture of SLSLSPGK (SEQ ID NO:4) and SLSLSPG (SEQ ID NO:3) was quantified by UV chromatography, as shown in FIG. 4A. Corresponding K AUC/des-K AUC values for PGK peptides were 1.08. Similarly, K AUC/des-K AUC values for LGK peptides were 1.07. Equimolar amounts of the SLSLSPGK (SEQ ID NO:4) and SLSLSPG (SEQ ID NO:3) reagent set were quantified by XIC, as shown in FIG. 4B. Heavy AUC/light AUC values for PGK and LGK peptides are shown in Table 1.

TABLE 1

| Peptide | Heavy/light isotope | Heavy AUC/ light AUC |
|---|---|---|
| SLSLSPGK (SEQ ID NO: 4) | Δ4/Δ0 | 0.98 |
|  | Δ8/Δ0 | 1.00 |
|  | Δ12/Δ0 | 0.99 |
|  | Δ16/Δ0 | 1.00 |
| SLSLSPG (SEQ ID NO: 3) | Δ4/Δ0 | 0.99 |
| SLSLSLGK (SEQ ID NO: 2) | Δ4/Δ0 | 1.02 |
|  | Δ8/Δ0 | 1.04 |
|  | Δ12/Δ0 | 1.06 |
|  | Δ16/Δ0 | 1.03 |
| SLSLSLG (SEQ ID NO: 1) | Δ4/Δ0 | 1.00 |

As shown in Table 1, the signals of the heavy peptides were approximately equal to the corresponding light peptides, validating the use of the heavy peptides in generating a calibration curve that can be applied to light peptides.

To determine the accuracy of the method, known quantities of light des-K and K were spiked into the reagent sets across the 1:10-1:1000 K to des-K peptide ratio range and measured using the calibration curve corrected method. As shown in Table 2, the calibration curve corrected values (or "normalized" values) were closely aligned with the expected percent lysine.

TABLE 2

| | SLSLSLGK (SEQ ID NO: 2) | | | SLSLSPGK (SEQ ID NO: 4) | |
|---|---|---|---|---|---|
| Expected % K | CC Corrected % K | % Difference | | CC Corrected % K | % Difference |
| 50.0 | 49.6 | 0.8 | | 50.8 | 1.5 |
| 9.1 | 8.9 | 2.0 | | 9.3 | 2.5 |
| 1.0 | 0.9 | 8.9 | | 1.0 | 7.1 |
| 0.1 | 0.1 | 2.0 | | 0.1 | 3.5 |

Example 2. Unprocessed C-Terminal Lysine Quantification of mAbs

This example shows the experimental design of the assay of the invention for accurate quantitation of C-terminus lysine (K) of a recombinant protein.

For antibody analysis, the calibration curves were spiked into antibody digests so that an approximately equimolar amount of heavy des-K peptide to digested des-K peptide was injected onto the column in each LC-MS/MS run.

Antibody Digestion.

Equal weights of five IgG4 mAb samples were buffer exchanged into 5 mM acetic acid and 5 mM TCEP-HCl before denaturation and reduction at 80° C. for ten minutes. The samples were further denatured in 4 M urea/0.1 M Tris-HCl, pH 7.5, and alkylated with 5 mM IAM at room temperature in the dark for 30 minutes. Urea concentration was lowered to 1 M by adding 0.1 M Tris-HCl, pH 7.4, and the antibodies were digested at a 1:20 antibody to trypsin ratio at 37° C. for 4 hours. Enzymatic activity was quenched by acidifying the samples in 0.2% TFA.

LC-MS and LC-MS/MS Parameters.

Aliquots of 5 μg of antibody digest were injected onto a 2.1 mm×150 mm Waters Acquity Ultra Performance Liquid Chromatography (UPLC) Charged Surface Hybrid (CSH) C18 column with 1.7 μm particles. Peptides were separated on this column with a Waters Acquity I-Class UPLC set to a flow rate of 250 μL/min and column temperature of 40° C. The gradient consisted of a 0.1-35% increase of organic mobile phase (ACN and 0.1% FA) relative to water and 0.1% FA over 95 minutes.

Mass data was acquired using a Thermo Q-Exactive Plus using QE Plus 3 and 4 systems and/or Orbitrap Fusion Lumos mass spectrometer. Full mass scans were performed on the Q-Exactive Plus acquiring an m/z range of 300-2000 at 140,000 resolution (m/z 200) for an ion population limited by an automatic gain control (AGC) target set to 1×106 or a maximum ion injection time (max IT) of 50 ms.

For experiments requiring MS/MS identification by data dependent acquisition (DDA), a single dd-MS/MS loop began by isolating and fragmenting each of the five most intense peptide ions with a 1.5 Th window using higher energy collisional dissociation (HCD) at a normalized collision energy of 30.

Fragment ion population data was collected using an AGC target of 1×105 or a max IT of 100 ms and then scanned at 17,500 resolution, at which point the sampled precursor was placed on an exclusion list for 10 seconds to ensure the analysis of less intense ions.

Orbitrap Fusion Lumos parameters for MS acquisition were the same as for the QE-Plus, with the exceptions being resolution set to 120,000 (m/z 200) and ACG target to 5×105. Differences in MS/MS settings were as follows: limiting DDA by a cycle time of one second instead of by number of precursors; setting AGC target to 2×104; controlling max IT with 50 ms but allowing for continued injection if parallelizable time was available; and scanning at 15,000 resolution (m/z 200).

Relevant LC-MS/MS raw files were analyzed with Byonic 3.0 using custom fasta files for each antibody according to the following parameters: (1) Cleavage Sites: R, K; (2) Cleavage Side: C-terminal; (3) Digestion Specificity: Fully Specific; (4) Precursor Mass Tolerance: 10 ppm; (5) Fragmentation Type: QTOF/HCD; (6) Fragment Mass Tolerance: 20 ppm; (7) Fixed and Variable Modifications: Fixed C Carbamidomethyl, Variable M Oxidation, Variable E/Q to pE, and Variable C-term K Loss; and (8) Glycan Modifications: 50 common biantennary N-glycans. Ion chromatograms for the 1+ and 2+ charge states of light and heavy C-terminal peptides were extracted in Thermo Xcalibur 3.1 by the Genesis algorithm set to a 10 ppm m/z tolerance. Quantitative AUC measurements were exported to Microsoft Excel, where calibration curves ranging from 1:1000-1:1 K to des-K were constructed to calculate the percentage of unprocessed C-terminal K in each sample.

Table 3 shows the results obtained using the calibration curve correction method compared to normal, uncorrected peptide mapping. As shown in Table 3, the percentage of C-terminal lysine is overestimated during peptide quantification using uncorrected peptide mapping in comparison to the calibration curve (CC) corrected method of the present disclosure. Thus, the method of the present invention provides a critical correction for quantification of a recombinant protein PTM, for example, C-terminal lysine of an antibody.

TABLE 3

| | CC Corrected C-term Lys % | | Uncorrected C-term Lys % | |
|---|---|---|---|---|
| Antibody | Mean | Standard Deviation | Mean | Standard Deviation |
| mAb 1 | 5.7 | 0.2 | 10.4 | 0.4 |
| mAb 2 | 6.9 | 0.7 | 11.5 | 0.7 |
| mAb 3 | 6.3 | 0.2 | 12.0 | 0.3 |
| mAb 4 | 9.8 | 0.4 | 15.8 | 0.2 |
| mAb 5 | 11.8 | 0.4 | 19.1 | 1.1 |

Example 3. Unprocessed C-Terminal Lysine Quantification of Bispecific Antibodies (BsAbs)

This example shows the experimental design of the assay of the invention for accurately quantifying PTMs of bispecific antibodies (bsAbs).

Seven IgG4-based bsAbs, containing both SLSLSLGK (SEQ ID NO:2) and SLSLSPGK (SEQ ID NO:4) C-terminal sequences, were digested as described above. Calibration curves were spiked into the antibody digests and approximately equimolar amount of heavy des-K peptide to digested des-K peptide was injected onto the column in each LC-MS/MS run. Control bsAb digests were subjected to traditional, uncorrected peptide mapping.

Table 4 shows the results obtained using the calibration curve correction method compared to normal, uncorrected peptide mapping of the PGK C-terminal sequences. As shown in Table 4, the percentage of C-terminal lysine is significantly overestimated during peptide quantification using uncorrected peptide mapping in comparison to the CC corrected method of the present disclosure.

TABLE 4

| Antibody (PGK) | CC Corrected C-term Lys % | | Uncorrected C-term Lys % | |
|---|---|---|---|---|
| | Mean | Standard Deviation | Mean | Standard Deviation |
| bsAb 1 | 14.3 | 0.1 | 23.9 | 0.3 |
| bsAb 2 | 15.3 | 0.0 | 23.5 | 0.6 |
| bsAb 3 | 15.8 | 0.0 | 27.3 | 1.0 |
| bsAb 4 | 16.4 | 0.2 | 27.0 | 0.5 |
| bsAb 5 | 16.9 | 0.2 | 25.7 | 1.2 |
| bsAb 6 | 20.0 | 0.1 | 30.1 | 0.6 |
| bsAb 7 | 26.4 | 0.3 | 37.3 | 0.3 |

Table 5 shows the results obtained using the calibration curve correction method compared to uncorrected peptide mapping of the LGK C-terminal sequences. As shown in Table 5, the percentage of C-terminal lysine is significantly overestimated during peptide quantification using uncorrected peptide mapping in comparison to the CC corrected method of the present disclosure.

TABLE 5

| Antibody (LGK) | CC Corrected C-term Lys % | | Uncorrected C-term Lys % | |
|---|---|---|---|---|
| | Mean | Standard Deviation | Mean | Standard Deviation |
| bsAb 1 | 2.0 | 0.1 | 3.5 | 0.1 |
| bsAb 2 | 2.5 | 0.1 | 4.1 | 0.1 |
| bsAb 3 | 2.2 | 0.1 | 3.7 | 0.2 |
| bsAb 4 | 2.5 | 0.2 | 4.2 | 0.1 |
| bsAb 5 | 2.7 | 0.0 | 4.7 | 0.1 |
| bsAb 6 | 3.4 | 0.1 | 5.7 | 0.1 |
| bsAb 7 | 5.1 | 0.1 | 8.4 | 0.2 |

Further experiments were carried out to investigate variation in quantitation between instruments when employing the method of the invention. Five IgG4 mAbs and one IgG1 mAb were digested as described above. Calibration curves were spiked into the antibody digests and approximately equimolar amount of heavy des-K peptide to digested des-K peptide was injected onto the column in each LC-MS/MS run. Control mAb digests were subjected to traditional, uncorrected peptide mapping. Mass data were acquired using a Thermo Q-Exactive Plus and an Orbitrap Fusion Lumos mass spectrometer.

As shown in Table 6, when using the CC corrected method, there was zero to little difference in percent lysine when quantified using either the QE-Plus or Fusion mass spectrometer. However, greater variability of percent lysine was seen across instruments when uncorrected peptide mapping was used.

TABLE 6

| Antibody (C-term) | CC Corrected C-term Lys % | | | Uncorrected C-term Lys % | | |
|---|---|---|---|---|---|---|
| | QE-Plus | Fusion | % RSD | QE-Plus | Fusion | % RSD |
| IgG4 mAb 1 | 5.5 | 5.5 | 0.4 | 10.0 | 9.1 | 6.5 |
| IgG4 mAb 2 | 6.5 | 6.5 | 0.2 | 10.9 | 9.8 | 7.5 |
| IgG4 mAb 3 | 6.6 | 6.5 | 0.7 | 12.2 | 10.0 | 14.0 |
| IgG4 mAb 4 | 9.7 | 9.6 | 0.7 | 16.0 | 14.8 | 5.5 |
| IgG4 mAb 5 | 12.0 | 11.6 | 2.6 | 20.0 | 17.7 | 8.8 |
| IgG1 mAb 1 (PGK) | 0.7 | 0.6 | 8.6 | 1.1 | 0.8 | 19.2 |

Additional experiments were carried out to investigate signal variability due to instruments using the method of the invention when applied to bsAbs. Seven IgG4-based bsAbs (containing both SLSLSLGK (SEQ ID NO:2) and SLSL-SPGK (SEQ ID NO:4) C-terminal sequences) were digested as described above. Calibration curves were spiked into the antibody digests and approximately equimolar amounts of heavy des-K peptide to digested des-K peptide was injected onto the column in each LC-MS/MS run. Control bsAb digests were subjected to traditional, uncorrected peptide mapping.

Mass data were acquired using a Thermo Q-Exactive Plus and an Orbitrap Fusion Lumos mass spectrometer. As shown in Table 7, when using the CC corrected method, there was zero to little difference in percent lysine when quantified using either the QE-Plus or Fusion mass spectrometer. However, greater variability of percent lysine was seen across instruments when uncorrected peptide mapping was used.

TABLE 7

| Antibody | C-terminal | CC Corrected C-term Lys % | | | Uncorrected C-term Lys % | | |
|---|---|---|---|---|---|---|---|
| | | QE-Plus | Fusion | % RSD | QE-Plus | Fusion | % RSD |
| bsAb 1 | PGK | 14.2 | 14.8 | 2.7 | 24.1 | 18.9 | 17.0 |
| | LGK | 2.1 | 2.1 | 2.6 | 3.6 | 3.2 | 9.2 |
| bsAb 2 | PGK | 15.3 | 15.5 | 1.2 | 24.2 | 19.2 | 16.3 |
| | LGK | 2.6 | 2.5 | 2.5 | 4.0 | 4.2 | 3.3 |
| bsAb 3 | PGK | 15.8 | 16.3 | 2.2 | 28.1 | 20.8 | 20.9 |
| | LGK | 2.3 | 2.2 | 3.8 | 3.7 | 3.3 | 7.7 |
| bsAb 4 | PGK | 16.3 | 16.9 | 2.2 | 28.1 | 20.8 | 20.9 |
| | LGK | 2.6 | 2.5 | 2.1 | 4.3 | 3.9 | 6.2 |
| bsAb 5 | PGK | 16.7 | 17.3 | 2.2 | 24.8 | 21.1 | 11.4 |
| | LGK | 2.7 | 2.7 | 1.2 | 4.6 | 4.3 | 4.2 |
| bsAb 6 | PGK | 20.1 | 20.4 | 1.3 | 30.6 | 25.1 | 14.0 |
| | LGK | 3.5 | 3.4 | 2.6 | 5.8 | 5.3 | 6.0 |
| bsAb 7 | PGK | 26.1 | 26.9 | 2.0 | 37.6 | 31.9 | 11.8 |
| | LGK | 5.2 | 5.1 | 0.9 | 8.6 | 8.0 | 5.0 |

What is claimed is:

1. A method for quantifying a post-translational modification of a protein of interest, comprising:
   (a) contacting a sample including said protein of interest to a digestive enzyme to obtain a peptide digest;
   (b) adding to said peptide digest a set of heavy peptide standards, wherein at least one heavy peptide standard includes said post-translational modification and at least one heavy peptide standard does not include said post-translational modification;
   (c) subjecting said peptide digest with said added heavy peptide standards to analysis using liquid chromatography-mass spectrometry to acquire a signal corresponding to each peptide of the peptide digest and heavy peptide standards;
   (d) generating a calibration curve using a relative signal of the at least one heavy peptide standard including said post-translational modification compared to the at least one heavy peptide standard not including said post-translational modification;
   (e) quantifying a post-translational modification of said protein of interest using the relative signal of at least one peptide from said protein of interest including said post-translational modification compared to at least one peptide from said protein of interest not including said post-translational modification; and
   (f) normalizing the result of (e) using the calibration curve of (d) to further quantify said post-translational modification of said protein of interest.

2. The method of claim 1, wherein the protein of interest is a therapeutic protein.

3. The method of claim 2, wherein said therapeutic protein is selected from a group consisting of an antibody, a soluble receptor, an antibody-drug conjugate, and an enzyme.

4. The method of claim 1, wherein said protein of interest is a monoclonal antibody.

5. The method of claim 1, wherein said protein of interest is a bispecific antibody.

6. The method of claim 1, wherein said post-translational modification is the presence of an unprocessed C-terminal lysine.

7. The method of claim 1, wherein said heavy peptide standards are present at molar ratios between about 1:1 and about 1:1000 relative to at least one other heavy peptide standard.

8. The method of claim 1, wherein said heavy peptide standards comprise between about 1 and about 16 heavy isotopes.

9. The method of claim 1, where said heavy peptide standards comprise $C^{13}$, $N^{15}$, or a combination thereof.

10. The method of claim 1, wherein said digestive enzyme is trypsin.

11. The method of claim 1, wherein said liquid chromatography method comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

12. The method of claim 1, wherein said mass spectrometer is an electrospray ionization mass spectrometer, nano-electrospray ionization mass spectrometer, comprising an Orbitrap mass spectrometer, a Q-TOF mass spectrometer or a triple quadrupole mass spectrometer, wherein said mass spectrometer is coupled to said liquid chromatography system, and wherein said mass spectrometer is capable of performing LC-MS, LC-MRM-MS, and/or LC-MS/MS analyses.

\* \* \* \* \*

SEQUENCE LISTING

<160> NUMBER OF SEQ ID NOS: 4

<210> SEQ ID NO 1
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 1

Ser Leu Ser Leu Ser Leu Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Leu Ser Leu Ser Leu Gly Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Leu Ser Leu Ser Pro Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Leu Ser Leu Ser Pro Gly Lys
1               5
```